US008795655B2

(12) United States Patent
Senga et al.

(10) Patent No.: US 8,795,655 B2
(45) Date of Patent: Aug. 5, 2014

(54) THERAPEUTIC AGENT FOR A LOWER URINARY TRACT DISEASE AND AN AGENT FOR IMPROVING A LOWER URINARY TRACT SYMPTOM (75) Inventors: Hirobumi Senga, Chiyoda-ku (JP); Yongling Wan, Beijing (CN); Masato Honma, Ome (JP)

(73) Assignee: Tobishi Pharmaceutical Co., Ltd., Chiyoda-ku, Tokyo (JP)

( * ) Notice: Subject to any disclaimer, the term of this patent is extended or adjusted under 35 U.S.C. 154(b) by 243 days.

(21) Appl. No.: 12/996,495

(22) PCT Filed: Jul. 1, 2009

(86) PCT No.: PCT/JP2009/062402
§ 371 (c)(1),
(2), (4) Date: Dec. 6, 2010

(87) PCT Pub. No.: WO2010/002035
PCT Pub. Date: Jan. 7, 2010

(65) Prior Publication Data
US 2011/0150858 A1 Jun. 23, 2011

(30) Foreign Application Priority Data

Jul. 1, 2008 (JP) .................................. 2008-172611

(51) Int. Cl.
*A61K 38/48* (2006.01)
(52) U.S. Cl.
USPC .......................... 424/94.64; 435/183; 424/542
(58) Field of Classification Search
None
See application file for complete search history.

(56) References Cited

U.S. PATENT DOCUMENTS

| | | | |
|---|---|---|---|
| 4,137,127 | A | 1/1979 | Stocker |
| 5,990,114 | A | 11/1999 | Leonardi et al. |
| 6,685,745 | B2 | 2/2004 | Reever |
| 7,335,668 | B2 | 2/2008 | Ikeda et al. |
| 7,485,151 | B2 | 2/2009 | Reever |
| 8,034,119 | B2 | 10/2011 | Reever |
| 8,231,870 | B2 | 7/2012 | Desser |
| 2002/0173818 | A1 | 11/2002 | Reever |
| 2004/0127996 | A1 | 7/2004 | Reever |
| 2007/0099986 | A1 | 5/2007 | Ishichi et al. |
| 2009/0164025 | A1 | 6/2009 | Reever |
| 2010/0254968 | A1 | 10/2010 | Desser et al. |

FOREIGN PATENT DOCUMENTS

| | | |
|---|---|---|
| JP | 2011-505385 | 2/2011 |
| WO | WO 02/091957 A1 | 11/2002 |
| WO | WO 2007/037561 A1 | 4/2007 |
| WO | WO 2009/070818 A1 | 6/2009 |

OTHER PUBLICATIONS

Zhong et al., China Pharmacy, 2000, 03, Abstract Only.*
Schneider et al., BJU International, 2005, vol. 95, p. 238-243.*
Asfaha et al., British Journal of Pharmacology, 2007, vol. 150, p. 176-185 (published online on Dec. 18, 2006).*
International Search Report (PCT/ISA/210) issued on Aug. 25, 2009, by Japanese Patent Office as the International Searching Authority for International Application No. PCT/JP2009/062402.
Written Opinion (PCT/ISA/237) issued on Aug. 25, 2009, by Japanese Patent Office as the International Searching Authority for International Application No. PCT/JP2009/062402.
Sakuma, H. et al., The clinical effect of factor XIII on drug-induced hemorrhagic cystitis, Rinsho Ketsueki, 1994, vol. 35, No. 3, p. 279-285.
Paul Abrams et al., The Standardisation of Terminology of Lower Urinary Tract Function: Report from the Standardisation Sub-committee of the International Continence Society, Neurourology and Urodynamics 21, 167-178, 2002.
Anthony J. Schaeffer et al., Chapter 8 Infections of the Urinary Tract, Bladder Infections Uncomplicated Cystitis, in Campbell-Walsh Urology, 9th ed., Elsevier, Philadelphia 2007, pp. 254-259.
Philip M. Hanno, Md. MPH, Chapter 10, Painful Bladder Syndrome-Interstitial Cystitis and Related Disorders, in Campbell-Walsh Urology, 9th ed., Elsevier, Philadelphia, 2007, pp. 330-349.
J. Curtis Nickel et al., Chapter 23 Prostatitis, Orchitis, and Epididymitis: Prostatitis, in Diseases of the Kidney and Urinary Tract, 8th ed. Lippincott Williams & Wilkins, Philadelphia, 2007, pp. 634-649.
Zermann DH et al, Chapter 22, Disorders of Micturition: Treatment of Lower Urinary Tract Dysfunction, in Diseases of the Kidney and Urinary Tract, 8th ed., Lippincott Williams & Wilkins, Philadelphia, 2007, pp. 621-625.
Stocker KF, Snake venom proteins affecting hemostasis and fibrinolysis, in Medical Use of Snake Venom Proteins, Stocker KF, ed., CRC Press, Boston, 1990, pp. 130-131.
D.L. Aronson, Comparison of the Actions of Thrombin and the Thrombin-Like Venom Enzymes Ancrod and Batroxobin, Thrombos Haemostas (Stuttg.) 36, 1976, pp. 9-13.
Nobuyuki Itoh et al., Molecular Cloning and Sequence Analysis of cDNA for Batroxobin, a Thrombin-like Snake Venom Enzyme, The Journal of Biological Chemistry, vol. 262, No. 7, Mar. 5, 1987, pp. 3132-3135.
Stocker KF, Snake venom proteins affecting hemostasis and fibrinolysis, in Medical Use of Snake Venom Proteins, Stocker KF, ed., CRC Press, Boston, 1990, pp. 134-135.
Stocker KF, Snake venom proteins affecting hemostasis and fibrinolysis, in Medical Use of Snake Venom Proteins, Stocker KF, ed., CRC Press, Boston, 1990, pp. 140-141.
Masaaki Ishikawa et al., Drug Interaction Effects on Antitumour Drugs (XV): Disulfiram as Protective Agent Against Cyclophosphamide-Induced Urotoxicity Without Compromising Antitumour Activity in Mice, Pharmacology & Toxicology 1994, 74, pp. 255-261.

(Continued)

*Primary Examiner* — Kade Ariani
(74) *Attorney, Agent, or Firm* — Buchanan Ingersoll & Rooney PC (57) ABSTRACT

The present invention provides a therapeutic agent for a lower urinary tract disease such as cystitis, interstitial cystitis, prostatitis, benign prostatic hyperplasia etc., which are considered as refractory disease, and an agent for improving a lower urinary tract symptom associated with the lower urinary tract disease.

9 Claims, 3 Drawing Sheets

(56) References Cited

OTHER PUBLICATIONS

Agnes Rouleau et al., Anti-Inflammatory and Antinociceptive Properties of BP 2-94, a Histamine $H_3$-Receptor Agonist Prodrug, Journal of Pharmacology and Experimental Therapeutics, vol. 295, No. 1, 2000, pp. 219-225.

Li-Yuan Yu-Lee, Prolactin Modulation of Immune and Inflammatory Responses, The Endocrine Society, 2002, pp. 435-455.

Michael P. O'Leary et al., The Interstitial Cystitis Symptom Index and Problem Index, Urology 49 (Supplement 5A), May 1997, pp. 58-63.

Extended European Search Report dated Jun. 18, 2012, issued in corresponding European Patent Application No. 09773613.6-2107/2318038. (8 pages).

Japanese Office Action mailed on Aug. 5, 2013, issued in corresponding JP Patent Application No. 2010-545294.

Russian Office Action mailed on Jul. 12, 2013, issued in corresponding Russian Application No. 2011103445/15 (004733).

Pirkle, *Thrombin-like Enzymes from Snake Venoms: An Updated Inventory*, 79 Thromb Haemost 675-683 (1998).

\* cited by examiner

THERAPEUTIC AGENT FOR A LOWER URINARY TRACT DISEASE AND AN AGENT FOR IMPROVING A LOWER URINARY TRACT SYMPTOM

CROSS-REFERENCE TO RELATED APPLICATIONS

This application is a U.S. National Stage patent application pursuant to 35 U.S.C. §371 of International Patent Application PCT/JP2009/062402, filed on Jul. 1, 2009, which claims priority to Japanese Patent Application 2008-172611, filed on Jul. 1, 2008.

TECHNICAL FIELD

The present invention relates to a therapeutic agent for a lower urinary tract disease, wherein the agent comprises a thrombin-like enzyme and an agent for improving a lower urinary tract symptom associated with the lower urinary tract disease, wherein the agent comprises a thrombin-like enzyme.

BACKGROUND ART

Lower urinary tract consists of bladder and urethra. The lower urinary tract has the function of collecting urine in the bladder and the function of expelling the collected urine. At the 2002 International Continence Society, it was suggested to define abnormality of the lower urinary tract as lower urinary tract dysfunction and to define various symptoms caused by the result of the lower urinary tract dysfunctions as lower urinary tract symptoms.

Lower urinary tract symptoms are roughly divided into 3 categories: storage symptoms, voiding symptoms, and post micturition symptoms (Abrams P et al.: The Standardisation of Terminology of Lower Urinary Tract Function. Neurourology and Urodynamics 21:167-178, 2002).

Storage symptoms are those wherein urine does not accumulate in the bladder, or what is known as frequent urination (pollakiuria) or urinary incontinence.

The following examples of the storage symptoms are included below.
1) Increased daytime frequency: the voicing in the daytime occurs too often.
2) Nocturia: the individual must wake up at night one or more times in order to void.
3) Urgency: sudden compelling desire to pass urine, which is difficult to defer.
4) Urinary incontinence: involuntary leaking of urine.
5) Urge urinary incontinence: involuntary leakage of urine accompanied by or immediately preceded by urgency.
6) Stress urinary incontinence: involuntary leakage of urine that occurs on abdominal pressure, or on coughing and sneezing.
7) Mixed urinary incontinence: a combination of urge urinary incontinence and stress urinary incontinence are experienced.

Voiding symptoms are experienced during the voiding phase, and are pointed out to be symptoms in which voiding is difficult. Specifically, the following symptoms are included.
1) Slow stream: reduced urine flow.
2) Splitting: urine stream splits.
3) Intermittent stream: urine stream stops and starts more than once during micturition.
4) Hesitancy: a delay in the onset of voiding after the individual is ready to pass urine.
5) Straining: abdominal pressure is needed to initiate, maintain, or improve the urinary stream.
6) Terminal dribble: the termination of micturition is prolonged and the urine flow slows to a dribble.

Post micturition symptoms are symptoms seen immediately after micturition. Specific examples of the following are included.
1) Feeling of incomplete emptying: the feeling that the bladder has not been completely emptied after passing urine.
2) Post micturition dribble: the involuntary loss of urine immediately after voiding; Males will experience this symptom immediately after leaving the toilet whereas females will experience this symptom after rising from the toilet.

Moreover, genitourinary pain and lower urinary tract pain are mentioned under the lower urinary tract symptoms category, as symptoms alongside the above-mentioned storage symptoms, voiding symptoms, and post micturition symptoms in the above article (Abrams P et al.: The Standardisation of Terminology of Lower Urinary Tract Function. Neurourology and Urodynamics 21:167-178, 2002).

From the above article, examples of lower urinary tract pain include the following symptoms:
1) Bladder pain: the pain felt in the suprapubic region and retropubic region. Bladder pain usually increases with bladder filling, and may persist after micturition.
2) Urethral pain: pain felt in the urethral area.

A lower urinary tract disease generally means all diseases which cause a lower urinary tract symptom and includes various functional disorders and diseases in the bladder, the prostate gland and the urethra. Specifically, the diseases in females occur in areas such as the bladder and urethra, while the diseases in males occur in the areas such as the bladder, urethra and also in the prostate gland.

Diseases of the bladder include, for example, uncomplicated cystitis, hemorrhagic cystitis, interstitial cystitis, bladder neck sclerosis, neuropathic bladder, contracted bladder, overactive bladder, underactive bladder and other bladder-related diseases.

Diseases of the prostate gland include, for example, acute or chronic bacterial prostatitis, chronic nonbacterial prostatitis, benign prostate hyperplasia, other prostate-related diseases and the like.

Diseases in the urethra include, for example, urethritis and urethrostenosis and other urethra-related diseases.

Cystitis refers to infectious or non-infectious inflammation which mainly arises in the bladder mucous membrane and submucosal tissue. Clinically, storage symptoms, voiding symptoms, post micturition symptoms and lower urinary tract pain are observed. Generally cystitis is divided into acute and chronic form on the basis of clinical progress. Depending on the presence or absence of obstructive disease in the lower urinary tract, cystitis is classified into uncomplicated cystitis and complex cystitis. Generally uncomplicated cystitis proceeds acutely and responds well to antimicrobial drugs. Complex cystitis proceeds chronically and often does not respond well to antimicrobial drugs and is thus sometimes referred to as intractable cystitis. Intractable cystitis includes hemorrhagic cystitis, interstitial cystitis, bacterial intractable cystitis and eosinophilic cystitis (Schaeffer A J et al.: Chapter 8 Infections of the Urinary Tract, Bladder Infectious Uncomplicated Cystitis, in Campbell-Walsh Urology, 9th ed.: Elsevier, Philadelphia 254-259, 2007).

Hemorrhagic cystitis, which has symptoms of cystitis, is characterized primarily by the presence of heavy hematuria. It can be caused in a number of different ways.

Main causes are
1) Viruses such as adenovirus and influenza;
2) Microorganisms including bacteria such as *Escherichia cob*, *Proteus* and *Pseudomonas aeruginosa*;
3) Chemical stimulation by anticancer drugs such as cyclophosphamide;
4) Physical stimulation by radiation exposure and the like.

Interstitial cystitis is a disease of the bladder in which the main complaints include urgency, pollakiuria, lower abdominal pain and other complaints include incomplete bladder emptying, malaise and anxiety. The causes are thought to be derived from lymphatic system disorders, chronic infectious diseases, nervous system disorders, mental disorders, autoimmune disease, destruction of defense mechanism in the urinary bladder, mast cell and so on. However the true etiology is not clear (Hanno P M et al.: Chapter 10 Painful Bladder Syndrome/Interstitial Cystitis and Related Disorders, in Campbell-Walsh Urology, 9th ed. Elsevier, Philadelphia 330-349, 2007).

A typical form of bacterial intractable cystitis is bladder tuberculosis. Bladder tuberculosis exhibits clear symptoms of cystitis and pyuria; and conventional antibacterial drugs are not effective for treatment. Acid-fast stain and tubercle *bacillus* cultures are used to diagnose urinary tract tuberculosis. Cystoscopic examination reveals distinct yellow papule nodules and this was diagnosed as bladder tuberculosis. Treatment by administration of a tuberculostatic agent is effective.

Eosinophilic cystitis exhibits symptoms similar to those of acute bacterial cystitis and pyuria. However, the urine culture is negative and antimicrobial drugs are not effective. This pathological condition is caused by an allergic reaction against drugs with antiallergic properties. Typical examples of such drugs include Tranilast. But other antiallergic drugs may also induce cystitis. Pyuria contains mainly eosinophils. But when eosinophils are absent, polynuclear leucocytes and lymphocytes can be present. Eosinophilic cystitis could be alleviated by withdrawing the drugs which induced the symptoms. However, when the symptoms are difficult to alleviate, administration of steroids is performed.

Acute prostatitis is caused mostly by bacterial inflammation. Typical examples of inflammation-inducing bacteria include gram-negative rod-shaped bacteria, particularly *Escherichia coli*. When a patient with a history of urinary tract infections is affected with acute prostatitis, inflammation-inducing bacteria of the disease is gram-negative rod-shaped bacteria such as *Pseudomonas aeruginosa* and *Serratia* in the same manner as so-called complicated urinary tract infections. Moreover, although the occurrence is not high, *Enterococcus* and *Staphylococcus aureus* can be the inflammation-inducing bacteria present. Generally symptoms include lower urinary tract pain and high fever accompanied by shivering and chills. This is a pathological condition that can be easily diagnosed by the swelling of the prostate, tenderness and urinary findings (Nickel J C et al.: Chapter 23 Prostatitis, Orchitis, and Epididymitis: Prostatis, in Diseases of the Kidney and Urinary Tract, 8th ed. Lippincott Williams & Wilkins, Philadelphia, 634-649, 2007).

Chronic prostatitis is divided into chronic bacterial prostatitis and chronic nonbacterial prostatitis. In the clinical setting, voiding symptoms, post micturition symptoms and lower urinary tract pain are present. In severe cases, the urine storage ability is affected and storage symptoms are seen. It is thought that the route of infection of chronic bacterial prostatitis follows the same route as acute prostatitis; firstly where acute prostatitis becomes chronic and secondary where the chronic bacterial prostatitis proceeds from onset. Symptoms are the irritative symptoms that occur during micturition such as pollakiuria, feeling of incomplete emptying and lower urinary tract pain. The degree of these symptoms is lower than that of the acute stage. Cases of chronic nonbacterial prostatitis occur very frequently, yet the causes are not clearly understood. Chronic nonbacterial prostatitis cannot be distinguishable from bacterial prostatitis based on its symptoms and prostate palpation. When the preceding urinary tract infection is not observed and urinalysis and post-massage prostate fluid cannot verify the presence of bacteria, the presence of leukocytes is used to diagnose chronic nonbacterial prostatitis (Nickel J C et al.: Chapter 23 Prostatitis, Orchitis, and Epididymitis: Prostatis, in Diseases of the Kidney and Urinary Tract, 8th ed. Lippincott Williams & Wilkins, Philadelphia, 634-649, 2007).

Benign prostatic hyperplasia refers to a pathological condition in which hypofunction of the prostate due to aging induces formation of fibromuscular or glandular nodules on the glands surrounding the urethra. These nodules gradually enlarge resulting in an overall enlargement of the prostate. Benign prostatic hyperplasia itself is a benign disease. But when the disease progresses causing the prostate to expand, the disease causes the obstruction of the urinary tract, resulting in lower urinary tract dysfunctions and renal dysfunctions. Clinically, symptoms of benign prostatic hyperplasia mainly include voiding symptoms, post micturition symptoms and lower urinary tract pain. In severe cases, the urine collecting ability of the bladder is affected and storage symptoms are seen.

In recent years, due to an aging society, lower urinary tract symptoms and lower urinary tract pain pose big problems in nursing and clinical care. Lower urinary tract symptoms and lower urinary tract pain are considered to be caused by complicated causes such as cerebrovascular diseases and neurodegenerative diseases as well as lower urinary tract diseases.

So far some therapeutic agents for lower urinary tract diseases have already been introduced. For example there are alpha-1 blockers that treat hypofunction of micturition and benign prostatic hyperplasia such as tamsulosin and naftopidil; anticholinergics that treat pollakiuria and urinary incontinence such as oxybutynin hydrochloride and propiverine hydrochloride; and smooth muscle relaxants that treat pollakiuria and urgency such as flavoxate hydrochloride and the like (Zermann D H et al.: Chapter 22, Disorders of Micturition: Treatment of Lower Urinary Tract Dysfunction, in Diseases of the Kidney and Urinary Tract, 8th ed., Lippincott Williams & Wilkins, Philadelphia, 621-625, 2007).

In recent years, it has been reported a compound which has an affinity for a $5\text{-HT}_{1A}$ receptor and is effective in the treatment/prevention of lower urinary tract disease (U.S. Pat. No. 5,990,114). It has also been reported that a tetrahydroisoquinoline-derivative, which is an agent that depresses a capsaicin-sensitive sensory nerve, is effective on interstitial cystitis, hypersensitivity in the lower urinary tract and nonbacterial prostatitis (U.S. Pat. No. 7,335,668).

However, from the viewpoint of effectiveness and safety, the development of a new therapeutic agent for a lower urinary tract disease and a new agent for improving a lower urinary tract symptom still have been needed.

DISCLOSURE OF INVENTION

The object of the present invention is to provide a new therapeutic agent for lower urinary tract disease and an agent for improving a lower urinary tract symptom which are excellent in efficacy and safety.

Although the inventors of the present invention have examined the effectiveness of various drugs for the treatment of lower urinary tract diseases, the inventors discovered that a thrombin-like enzyme had surprisingly remarkable therapeutic effects on lower urinary tract disease and positive effects on improving the lower urinary symptom accompanying lower urinary tract diseases. The present invention is accomplished based on the above-mentioned findings.

Namely, the present invention provides a therapeutic agent for a lower urinary tract disease wherein the agent comprises a thrombin-like enzyme and an agent for improving a lower urinary tract symptom associated with lower urinary tract disease, wherein the agent comprises a thrombin-like enzyme.

As shown in Examples below, a therapeutic agent of the present invention for a lower urinary tract disease comprising a thrombin-like enzyme can treat various lower urinary tract diseases such as cystitis, prostatitis, and benign prostatic hyperplasia and can improve a lower urinary tract symptom associated with these diseases. Accordingly, the problems related to lower urinary tract symptoms that occur in nursing and clinical care can be overcome with use of the present invention.

BRIEF DESCRIPTION OF THE DRAWINGS

FIG. 2 (A) is a photomicrograph (×40) of the model group in the experiment on chronic nonbacterial prostatitis. A rightward arrow points to an infiltration of neutrophils in a glandular cavity.

FIG. 2 (B) is a photomicrograph (×40) of the model group in the experiment on chronic nonbacterial prostatitis. The leftward arrow points to the plasmacyte and lymphocyte infiltration into the stromata.

FIG. 5 (A) shows a photomicrograph (×40) of the model group in the experiment on benign prostatic hyperplasia. A rightward arrow shows a nipple-like thickening in the epithelial glands.

FIG. 5 (B) shows a photomicrograph (×40) of the model group in the experiment on benign prostatic hyperplasia. A leftward arrow shows the proliferation and fibrosis of the stromata.

BEST MODE FOR CARRYING OUT THE INVENTION

Hereinafter, the present invention will be explained in detail.

It should be understood that the terms in the specification are used to have the meanings commonly used in the art, unless otherwise stated. Therefore, unless otherwise defined, all the technical terms and scientific terms, which are used in the specification, have the same meanings as what are generally understood by a person skilled in the art to which the present invention pertains. If the meaning of a term defined in the specification is different from that commonly used in the art, the meaning defined in the specification should be used in preference to that commonly used in the art.

The definitions of terms used in the present specification are enumerated below.

The term "a thrombin-like enzyme" used in the specification refers to a protease other than thrombin which has the characteristic of coagulating fibrinogen. Specific examples of the thrombin-like enzyme include batroxobin, ancrod, crotalase, flavoxobin, asperase, acutin, botropase, clotase, gabonase, venzyme and the like. Thrombin-like enzymes are classified into 3 categories based on a site of cleavage in the substrate, fibrinogen: (i) a protease (such as batroxobin, ancrod and crotalase) that releases only fibrinopeptide A from fibrinogen to generate fibrin I; (ii) a protease (such as gabonase) that releases fibrinopeptide A and fibrinopeptide B from fibrinogen to generate fibrin II, which is also called fibrin; and (iii) a protease (such as venzyme) that mainly releases fibrinopeptide B from fibrinogen.

In the specification, the term "fibrin I" refers to a monomer generated when only fibrinopeptide A releases from fibrinogen. This fibrin I is also called as Des A fibrin. Moreover, the term "fibrinopeptide A" is a peptide corresponding to the 16 amino acids at the $NH_2$ terminal end of the Act chain of fibrinogen.

Moreover, in the specification, batroxobin, ancrod, crotalase, flavoxobin, asperase, acutin and the like are mentioned as an example of the protease which generates fibrin I from fibrinogen.

The preferable thrombin-like enzyme of the present invention contains batroxobin, ancrod and crotalase (Stocker K F: Snake venom proteins affecting hemostasis and fibrinolysis, in *Medical Use of Snake Venom Proteins*, Stocker K F, ed., CRC Press, Boston, p130-131; 1990).

Batroxobin is a thrombin-like enzyme derived from the venom of *Bothrops atrox moojeni*, and a glycoprotein having the molecular weight of about 36,000 Da. Batroxobin releases fibrinopeptide A from fibrinogen, to generate fibrin I (Aronson DL: Comparison of the actions of thrombin and the thrombin-like venom enzymes Ancrod and Batroxobin. Thrombos Haemostas (stuttg) 36:9-13, 1976). Moreover, the primary structure of batroxobin has already been determined, Batroxobin is single chain glycoprotein of 231 amino acids (Itoh N et al: Molecular cloning and sequence analysis of cDNA for batroxobin, a thrombin-like snake venom enzyme. J Biol Chem 262: 3132-3135, 1987).

Thrombin and batroxobin are similar enzymes based on their glycoprotein structures. However, thrombin is different from batroxobin on their cleaving site in fibrinogen. Batroxobin releases only fibrinopeptide A from fibrinogen to generate fibrin I. However, thrombin releases not only fibrinopeptide A but also fibrinopeptide B from fibrinogen, and generates fibrin (known as fibrin II). In addition, Batroxobin acts no other coagulation factors except for fibrinogen whereas thrombin acts on other coagulation factors in addition to fibrinogen.

Batroxobin is a known substance, and can be prepared according to the method described in U.S. Pat. No. 4,137,127. Batroxobin can be easily obtained from Tobishi Pharmaceuticals Co., Ltd (Tokyo, Japan) or its subsidiary, Beijing Tobishi Pharmaceuticals Co., Ltd., (Beijing, China).

Ancrod is a thrombin-like enzyme derived from the venom of *Agkistrodon rhodostoma*, and a glycoprotein having the molecular weight of about 35,400 Da. Ancrod is similar to batroxobin, in that they are both thrombin-like enzymes that release only fibrinopeptide A from fibrinogen to generate fibrin I (Stocker K F: Snake venom proteins affecting hemostasis and fibrinolysis, in *Medical Use of Snake Venom Proteins*, Stocker K F, ed., CRC Press, Boston, p134.135; 1990).

Crotalase is a thrombin-like enzyme derived from the venom of the *Crotalus adamanteus*, and a glycoprotein having the molecular weight of about 32,700 Da. Crotalase is similar to batroxobin in that they are both thrombin-like enzymes which release only fibrinopeptide A from fibrinogen to generate fibrin I (Stocker K F: Snake venom proteins affecting hemostasis and fibrinolysis, in *Medical Use of Snake Venom Proteins*, Stocker K F, ed., CRC Press, Boston, p140-141; 1990).

Of these thrombin-like enzymes mentioned above, batroxobin is particularly preferable. The thrombin-like enzymes above-mentioned such as batroxobin, ancrod and crotalase in the present invention can be a natural product or genetic recombinant product.

"Lower urinary tract disease" which is the target of the present invention, refers all diseases which bring about lower urinary tract symptoms. Examples are listed as a disease or a functional disorder, etc of the bladder, prostate gland and urethra.

Examples of bladder disease are cystitis, bladder neck sclerosis, neurogenic bladder, atrophic bladder, overactive bladder, underactive bladder and the like. Specific examples of cystitis are uncomplicated cystitis, hemorrhagic cystitis, interstitial cystitis and the like.

Diseases in a prostate gland are prostatitis, benign prostatic hyperplasia and the like. Specific examples of prostatitis are acute or chronic bacterial prostatitis, chronic nonbacterial prostatitis and the like.

Examples of diseases in the urethra are urethritis and urethrostenosis.

Among these, cystitis, prostatitis and benign prostatic hyperplasia are preferably treated by the present invention. Furthermore, hemorrhagic cystitis, interstitial cystitis, chronic nonbacterial prostatitis and benign prostatic hyperplasia are more preferably treated by the present invention.

The present invention can be used to treat lower urinary tract disease. Here in the term "therapeutic" includes not only to cure a disease but also to halt the progression of disease and prevent its manifestation.

"Lower urinary tract symptom that is associated with lower urinary tract diseases", which is the target of the present invention, refers to all the symptoms that are caused by lower urinary tract disease. Specific examples are storage symptoms, voiding symptoms, post micturition symptoms, lower urinary tract pain and the like.

Storage symptoms are increased daytime frequency, nocturia, urgency, urinary incontinence, urge urinary incontinence, stress urinary incontinence, mixed urinary incontinence and the like.

Voiding symptoms are slow stream, splitting, intermittent stream, hesitancy, straining, terminal dribble and the like.

Post micturition symptoms are feelings of incomplete emptying, post micturition dribble and the like.

Moreover, examples of lower urinary tract pain are bladder pain, urethral pain and the like.

The present invention can improve the lower urinary tract symptoms that is associated with lower urinary tract disease. The term "improvement" includes not only the complete remission from symptoms but alleviation of symptoms, remission of deterioration of symptoms, prevention of manifestation, improvement of the Quality Of Life (QOL) and the like.

Any formulation in the Japanese Pharmacopeia General Rules for Preparations can be applied to the formulation of the present agent. Examples are injections for direct application inside the body (including suspensions and emulsions); ointments (including fatty ointments, emulsion ointments (creams), water-soluble ointments, and the like), inhalants, liquids (including ophthalmic solutions, collunarium, and the like), suppositories, patches, poultices, lotions and other external formulations; and internal formulations including tablets (including sugar-, film-, and gelatin-coated), liquids, capsules, granules, powders (including grains), pills, syrups, troches, and the like. These formulations can be prepared by the methods described in the Japanese Pharmacopoeia General Rules for Preparations and the like.

Moreover, the present agent may contain a pharmaceutically acceptable solid or liquid carrier or interventional therapy base according to its pharmaceutical dosage form. Examples of the pharmaceutically acceptable solid or liquid carrier are a solvent, a stabilizer, a preservative, a solubilizing agent, an emulsifier, a suspending agent, a buffering agent, an isotonizing agent, a coloring agent, a thickener, an excipient, a lubricant, a binding agent, a disintegrating agent, a coating agent, a corrigent and the like. Specific examples of the carrier include water, lactose, sucrose, fructose, glucose, mannitol, sorbitol and other sugars and sugar alcohols, crystalline cellulose, methylcellulose, ethylcellulose, hydroxypropylcellulose, low substituted hydroxypropylcellulose, hydroxypropylmethylcellulose, hydroxypropylmethylcellulose phthalate, hydroxypropylmethylcellulose acetate succinate, carmellose, carmellose calcium, carmellose sodium, croscarmellose sodium, carboxymethylethylcellulose, cellulose acetate phthalate and other celluloses and related derivatives, corn starch, wheat starch, rice starch, potato starch, dextrin, pre gelatinized starch, partly pregelatinized starch, hydroxypropyl starch, sodium carboxymethyl starch, cyclodextrin, pullulan and other starches and related derivatives, agar, sodium alginate, acacia, gelatin, collagen, shellac, tragacanth, xanthan gum (natural), and other natural polymers (seaweeds, plant mucilage, proteins and the like), polyvinylpyrrolidone, aminoalkyl methacrylate copolymer, methacrylic acid copolymer, carboxyvinyl polymer, polyvinyl alcohol, dimethylpolysiloxane and other synthetic polymers, olive oil, cacao butter, carnauba wax, beef tallow, hydrogenated oil, soybean oil, sesame oil, camellia oil, paraffin, liquid paraffin, yellow beeswax, white petrolatum, coconut oil, microcrystalline wax and other oils and fats, stearic acid, aluminum stearate, calcium stearate, magnesium stearate, triethyl citrate, triacetine, medium chain triglyceride, hard fat, isopropyl myristate, and other fatty acids and derivatives thereof, glycerin, stearyl alcohol, cetanol, propylene glycol, macrogol and other alcohols and polyvalent alcohols, zinc oxide, dibasic calcium phosphate, precipitated calcium carbonate, synthetic aluminum silicate, silicic acid anhydride, kaolin, dried aluminum hydroxide gel, synthetic hydrotalcite, titanium oxide, talc, bentonite, magnesium aluminometasilicate, aluminum potassium sulfate, bismuth subgallate, bismuth subsalicylate, calcium lactate, sodium bicarbonate and other inorganic substances and metal salt compounds, sucrose esters of fatty acid, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and other surfactants, dyes, perfumes and the like.

Examples of interventional therapy bases include stents, artificial blood vessels, catheter, balloon and the like.

The administered dose and number of the present agent generally varies depending on the type of thrombin-like enzyme, the patient's weight, disease's properties and conditions, but is, for example 0.1-50 Batroxobin Units (hereinafter referred to as BU) of batroxobin, as the thrombin-like enzyme, can be administered once per day, in the case of an adult human being. The preferred dose for an adult human being is one dose every other clay (one dose is 1-20 BU). In the case of external preparations, the close is 0.01-500 mg per gram.

A batroxobin unit is a unit indicating the enzymatic activity of batroxobin; with 2 BU being the activity to achieve coagulation in 19.0±0.2 seconds when 0.1 ml of batroxobin solution is added to 0.3 ml of standard human plasma containing citric acid at 37° C.

Also when the thrombin-like enzyme, ancrod, is administered to an adult once a day, the usual dose is 0.01-10 IU/kg. Preferably dose should be 0.5 IU/kg.

The present agent can be administered to the subject by intravenous drip, intravenous injection, intraarterial injection, intramuscular injection, subcutaneous injection, intradermal injection, intracardiac injection, intraperitoneal injection, intrathecal injection, intrarectal administration, sublingual administration, nasal administration, percutaneous administration, inhalation or local administration into organs and/or tissues afflicted with lower urinary tract diseases of a formulation prepared by diluting a thrombin-like enzyme appropriately.

Generally, it is preferable to dilute a thrombin-like enzyme with 100 ml or more of physiological saline and to administer the prepared formulation into a subject by drip infusion for 1 hour or more.

The acute toxicity ($LD_{50}$ (BU/kg)) of batroxobin on mice, rats, rabbits and dogs is as follows in Table 1. The acute toxicity test was assessed by the intravenous administration of batroxobin.

TABLE 1

Acute toxicity of batroxobin (i.v.)

| Animal species | $LD_{50}$ value (BU/kg) |
|---|---|
| Mouse (ddy) | 192-210 |
| Rat (Wistar) | 105-110 |
| Rabbit (NW) | >300 |
| Dog (mongrel) | 190-208 |

Although the followings provide a detailed explanation of the present invention by indicating Formulation example and Examples thereof, the present invention is not limited to these Formulation example and Examples.

Formulation Example 1

Batroxobin preparation was manufactured into an injection having the following composition.

| | |
|---|---|
| Batroxobin (active ingredient) | 10 BU |
| Chlorobutanol (preservative) | 3 mg |
| Gelatin hydrolysate (stabilizer) | 0.1 mg |
| Sodium chloride (isotonic agent) | 9 mg |
| Hydrochloric acid (pH regulator) | q.s. |
| Distilled water for injection | up to 1 ml |
| Total volume | 1 ml |

Example 1

The Effect of Batroxobin on Hemorrhagic Cystitis

Cyclophosphamide (CYP) is one kind of anticancer drug, and hemorrhagic cystitis is known as the main clinical side effect. CYP is metabolized in the body to form a 4-hydroxy substance expressing the anticancer activity. The 4-hydroxy substance is then metabolized in order to create a metabolite, acrolein, in the urine. It has been reported that acrolein is an direct inflammatory agent and the acrolein stimulation to the inner wall of bladder causes hemorrhagic cystitis.

1. Experimental Method

Batroxobin (hereinafter referred to as DF-521) was used, which is a product of Tobishi Pharmaceutical Co., Ltd, Japan. Cyclosphosphamide monohydrate (CYP) and Formamide were used, which is a product of Sigma Co., Ltd, USA. Evans Blue (EB) was used, which is a product of Tokyo Chemical Industry Co., Ltd. Male ddY mice (Jla: ddY, Japan Laboratory Animals, Inc) with an approximate body weight of 25-30 g were used.

(1) Animal Group Division, Establishment of the Hemorrhagic Cystitis Model and Dosage Method Mice were divided into 4 groups: a normal group (6 mice), a model group (12 mice), a DF-521 10 BU/kg intravenous administration (i.v.) group (11 mice), and a DF-521 40 BU/kg intraperitoneal administration (i.p.) group (11 mice). The DF-521 10 BU/kg i.v. group had mice wherein the tail vein administration of 10 BU/kg of DF-521 was received. The DF-521 40 BU/kg i.p. group had mice wherein an intraperitoneal administration of 40 BU/kg of DF-521 was received. 30 minutes after being given DF-521, the mice were given an intraperitoneal dose of 200 mg/kg of CYP in order to setup the hemorrhagic cystitis model. 2.5 hours after CYP administration, 30 mg/kg of EB was injected into the tail vein. 30 minutes later, the animals were sacrificed by cervical dislocation and the relative bladder weight and the plasma-protein leakage in the urinary bladder were measured using the following method. Furthermore, the model group was administered physiological saline which is the same dosage as the DF-521 (10 ml/kg). 200 mg/kg of CYP was administered intraperitoneally after 30 minutes. Thereafter according to the time schedule for each measurement items, the same treatment was performed.

The normal group had the normal mice receiving no treatment.

(2) Measurement of Relative Weight of a Bladder and Plasma-Protein Leakage into the Bladder Evans blue (EB) method was carried out in view of the methods of Ishikawa et al. (Drug interaction effects on antitumour drugs (XV): Disulfuram as protective agent cyclophosphamide induced urotoxicity without compromising antitumour activity in mice. Pharmacology and Toxicology 74: 255-261, 1994) and Rouleau A et al. (Anti-inflammatory and Antinociceptive properties of BP 2-94, a histamine H3-receptor agonist prodrug. J Pharmacol Exp Ther. 295(1): 219-225, 2000). Namely, after a mouse was intraperitoneally injected with 200 mg/kg of CYP, 30 mg/kg of EB solution was injected intravenously into the tail vein. 30 minutes after the EB solution was administered, the animals were sacrificed by cervical dislocation and opened by the midline incision. The bladder tissue is carefully removed, and a vertical incision is made in the urethra. Foreign materials (crystal-like deposits) and urine were removed in order to measure the wet weight of the bladder. The relative weight of bladder was represented as bladder weight mg/100 g body weight. Immediately, the bladder was put into a sample tube having 0.5 ml of formamide solution. The sample tube was incubated for 18 hours at 45° C. in the bladder tissue. The dye which was leaked into the bladder tissue was extracted with formamide solution. The absorbance of the extract was measured at a wavelength of 620 nm (ImmunoReader). The absorbance of EB standard concentrated solution (0.1-100 µg/ml) previously determined at a wavelength of 620 nm, the standard curve was established. The EB concentration of every sample fluid was calculated from the standard curve. The EB content in the bladder was represented as "µg EB/bladder." This was an indicator of plasma-protein leakage in the bladder.

(3) Statistical Analysis

The result was expressed as Mean±Standard Deviation. After the test of drug administration group and the model group was analyzed using the Bartlett method, the non-parametric Dunnett method was used to correct unequal variances. Moreover, the test of two groups: the model and normal group was conducted using a F-test and after the variance analysis was unequal, the Welch test was conducted for correction for unequal variances. The difference between the groups was considered to be significant, when percentage of risk was less than 5% ($p<0.05$).

2. Results

The results of the effect of batroxobin (DF-521) on hemorrhagic cystitis through the i.v injection (10 BU/kg) and i.p. administration (40 BU/kg) are shown in Table 2.

TABLE 2

| Groups | n | Relative bladder weight (bladder weight mg/100 g body weight) | Inhibition rate (%) | Evans blue content in bladder (µgEB/bladder) | Inhibition rate (%) |
|---|---|---|---|---|---|
| Normal group | 6 | 77.2 ± 4.34 | | 0.3 ± 0.04 | |
| Model group | 12 | 165.5 ± 7.88[#] | | 12.9 ± 0.89[#] | |
| DF-521 10 BU/kg i.v. group | 11 | 122.5 ± 6.29* | 48.7 | 8.1 ± 0.71* | 38.1 |
| DF-521 40 BU/kg i.p. group | 11 | 118.3 ± 9.86* | 53.5 | 7.3 ± 0.85* | 44.4 |

[#]$p < 0.01$ Comparison with the normal group;
*$p < 0.01$ Comparison with the model group As shown in Table 2, the relative weight of the bladder of the model group increased significantly (about 2.1 times) compared that of the normal group. On the other hand, the DF-521 10 BU/kg i.v. group indicated a significant inhibition (48.7%) of the relative bladder weight ($p<0.01$). The DF-521 40 BU/kg i.p. group indicated a significant inhibition (53.5%) of the relative bladder weight ($p<0.01$). The Evans Blue content in the bladder of the model group displayed a significant increase (about 43 times) compared that of the normal group ($p<0.01$). On the other hand, the DF-521 10 BU/kg i.v group displayed a significant inhibition rate of 38.1% ($p<0.01$). Moreover, the DF-521 40 BU/kg i.p. group displayed significant ($p<0.01$) inhibition rate of 44.4%. Namely, the DF-521 10 BU/kg i.p. group and DF-521 40 BU/kg i.p. group had comparably similar effects against the increase in the relative bladder weight and the rise in plasma-protein leakage into bladder in hemorrhagic cystitis. Moreover, based on observations to the naked eye, the degree of hypertrophy due to the edema of the bladder wall was evident in the model group and hemorrhaging of the bladder mucosa was observed in all animals in the model group. Moreover, in most animals, the area of the hemorrhaging occupied 25% or more of the total area of the bladder mucosa. On the other hand, in the DF-521 40 BU/kg i.p. group, the hypertrophy due to the edema of the bladder wall was thinner than that of the model group and the degree of hypertrophy was somewhat lower than that of the model group.

It became clear from these results that batroxobin, whether either administered intraperitoneally or intravenously, clearly inhibits the increase in relative bladder weight and increase in plasma-protein leakage into bladder in hemorrhagic cystitis. Both the increase in the relative bladder weight and the plasma-protein leakage are indications of hemorrhagic cystitis. Therefore, it is understood from the results of the examples that batroxobin is effective in the therapy of cystitis. It is thought, based on the results of the example, batroxobin is effective in the improvement of lower urinary tract symptoms associated with cystitis (i.e., the storage symptoms, voiding symptoms and post micturition symptoms) and a lower urinary tract pain.

Example 2

Effect of Batroxobin on Chronic Nonbacterial Prostatitis

1. Experimental Method

Batroxobin (DF-521) was used, which is a product of Beijing Tobishi Pharmaceutical Co., Ltd., China Sesame oil and 17β-Estradiol ($E_2$) were used, which is products of Sigma Co., Ltd., USA $E_2$ was used for the establishment of chronic nonbacterial prostatitis model.

(1) Experimental Animals and Group Division 13-week-old male Wistar rats weighing 330-420 g were purchased from Beijing Vital River Laboratory Animal Co., Ltd., China. The rats were raised in SPF class rooms with a Temperature of 20-25° C., Relative Humidity of 40-70%, Light and Dark Cycle, (12 h/12 h). Solid feed sterilized with $^{60}Co$ and sterilized water were provided ad libitum (SPF class, Beijing Science Au Corporate Feed Co., Ltd., China). After being quarantined and habituated for one week, the rats were ready to be used for the experiments. 13-week-old male Wistar rats were divided into 3 groups (Sham operation, Model, DF-521 30 BU/kg), having a number of 11 rats in each group.

(2) Establishment of Chronic Nonbacterial Prostatitis Model and Dosage Method

The scrotums of rats in the sham operation group under ether anesthesia were only cut open (the first clay of the experiment) and the next day, 1 ml/kg of sesame oil was administered subcutaneously on their backs once a day for 31 consecutive days. Rats in the other two groups were castrated under ether anesthesia (the first day of the experiment) and the next day, 0.25 mg/ml/kg of $E_2$ was dissolved in sesame oil and subcutaneously administered on the backs of the rats once a day for 31 consecutive days. The chronic nonbacterial prostatitis model was created from therein.

From 17th day, the sham operation and model groups were intraperitoneally injected with 5 ml/kg saline solution once every other day. The DF-521 30 BU/kg group was given an intraperitoneal dose of DF-521 (30 BU/5 ml/kg) once every other clay for 15 days. During the whole 15 days, DF-521 was administered 8 times.

(3) Prostate Weight Measurement, Prolactin Concentration Measurement and Histopathological Examination On the 32nd day of the experiment, under ether anesthesia, an EDTA anticoagulant was used and blood was collected from the abdominal aorta. After separating plasma, prolactin in plasma was measured by a commercial ELISA kit. Still, the prostate was extracted, the prostate weight was measured, and "Prostate index" was determined as prostate mg/100 g body weight. The lateral lobe was sectioned from the prostate, formalin-fixed, paraffin-embedded sections were made according to the conventional method, and hematoxylin-eosin (HE) staining was conducted. Histopathological sections were examined under the microscope.

2. Results (1) Rat Prostate Weight and a Prostate Index

The results of prostate weight and prostate index of rats in each group are shown in Table 3.

TABLE 3

| Groups | Prostate weight (mg) | Prostate index (prostate mg/100 g body weight) |
|---|---|---|
| Sham operation group | 938.4 ± 133.7 | 194.7 ± 28.4 |
| Model group | 195.2 ± 35.2 | 55.5 ± 11.5 |
| DF-521 30 BU/kg group | 203.2 ± 23.0 | 58.8 ± 8.0 |

As shown in Table 3, the prostate weight (mg) and prostate index (prostate mg/100 g body weight) of the sham operation group was 938.4 and 194.7 respectively whereas the figures for the model group were 195.2 and 55.5. The figures in the model group are clearly lower than the sham operation group. On the other hand, a little improvement was seen in the DF-521 30 BU/kg group compared to the model group. The prostate weight and prostate index are indications of chronic nonbacterial prostatitis. Therefore, it is understood from the results of the examples that batroxobin is effective in the therapy of chronic nonbacterial prostatitis.

(2) The Effect of Batroxobin on Prolactin in Rat Plasma

The prolactin concentration in the rat plasma of each group was shown in Table 4.

TABLE 4

| Groups | Prolactin (ng/ml) |
|---|---|
| Sham operation group | 12.1 ± 4.0 |
| Model group | 20.7 ± 10.3 |
| DF-521 30 BU/kg group | 11.2 ± 2.6 |

As shown in Table 4, the prolactin content in plasma of the model group clearly increased compared to prolactin content in the sham operation group. On the other hand, the prolactin content of the DF-521 30 BU/kg group was approximately half of the prolactin content in the model group. Prolactin is a hormone secreted from the adenohypophysis which promotes lactation. In recent years, it has been reported that prolactin is secreted from organs and tissues other than pituitary gland and has various physiological activities. Prolactin is thought to play a role in prostatitis (Yu-Lee Ly: Prolactin modulation of immune and inflammatory responses. Recent Prog Horm Res. 57: 435.455, 2002). Therefore, according to the present examples, it is suggested that the action of batroxobin in decreasing the prolactin concentration in the plasma is most likely one of the mechanisms to inhibit prostatitis.

(3) Histopathological Findings of the Rat Prostate Gland

Figure 1:
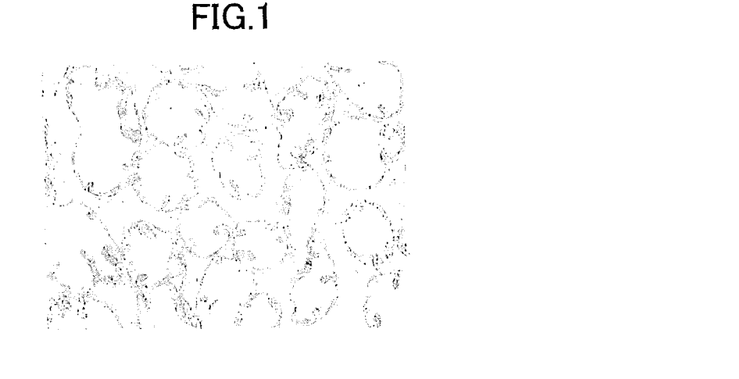
FIG. 1 is a photomicrograph (×40) of the sham operation group in the experiment on chronic nonbacterial prostatitis.
Figure 2:
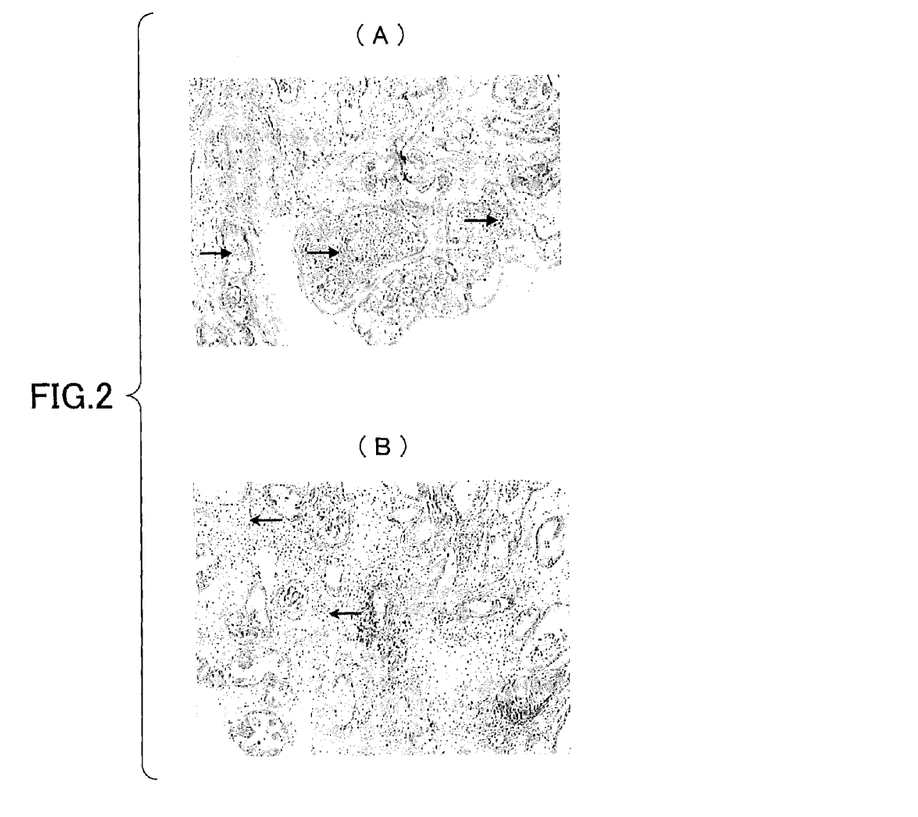
Figure 3:
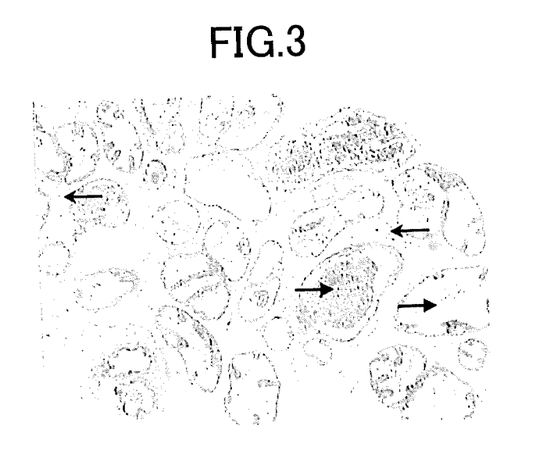
FIG. 3 is a photomicrograph (×40) of the DF-521 30 BU/kg group in the experiment on chronic nonbacterial prostatitis. A rightward arrow points to the reduction in infiltration of neutrophils into the glandular cavity. A leftward arrow points to the reduction in infiltration of lymphocytes and plasmacytes into the stromata.

FIG. 1 shows the sham operation group in the photomicrograph. In the sham operation group, the entire prostate was large. Individual glands had a rotund shape. In the glandular cavity, staining of rich secretory fluids were observed in the HE staining. FIG. 2 indicates the model group in the micrograph. The model group showed the prostate was irregularly shaped. There was heavy neutrophilic infiltration into the glandular cavity (Arrow, FIG. 2A). There was widespread, focal or scattered infiltration of lymphocytes and plasmacytes into the stroma (Arrow, FIG. 2B). Part of the glandular epithelium was necrotized and lost FIG. 3 shows a photomicrograph of the DF-521 30 BU/kg group. The neutrophil infiltration into the glandular cavity (Rightward arrow) and the lymphocyte and plasmacyte infiltration (Leftward arrow) were reduced compared to the model group. The glandular and stromal inflammation was clearly decreased. From these results, it can be understood that batroxobin is effective in treating chronic nonbacterial prostatitis.

(4) Semi-Quantitative Assessment Based on Histopathological Findings

The degrees of neutrophilic infiltration into glandular cavity and lymphocyte/plasmacyte infiltration into stroma in every rat prostate specimen were scored based on the following assessment criteria and then the effect of batroxobin on prostatitis was assessed.

The results are shown in Table 5. In Table 5, the value (%) for a group means a percentage of the number of rat having a score relative to the total number of rats in the group.

1) Assessment Criteria for Neutrophil Infiltration in the Glandular Cavity

0: No infiltration of neutrophils into the glandular cavity.
1: 24.9% or less of glands whose ⅓ or more of the area of glandular cavity was infiltrated by neutrophils.
2: 25-49.9% of glands whose ⅓ or more of the area of glandular cavity was infiltrated by neutrophils.
3: 50-74.9% of glands whose ⅓ or more of the area of glandular cavity was infiltrated by neutrophils.
4: 75% or more of glands whose ⅓ or more of the area of glandular cavity was infiltrated by neutrophils.

2) Assessment Criteria for Infiltration of the Lymphocytes and Plasmacytes into the Stroma.

0: no infiltration of lymphocytes and plasmacytes into the stroma.
1: scattered infiltration of lymphocytes and plasmacytes into the stroma.
2: focal infiltration of lymphocytes and plasmacytes into the stroma
3: widespread infiltration of lymphocytes and plasmacytes into the stroma.

TABLE 5

| | Neutrophilic infiltration into the glandular cavity (%) | | | Lymphocyte and plasmacyte infiltration into the stroma (%) | | |
|---|---|---|---|---|---|---|
| Score | Sham operation group | Model group | DF-521 30 BU/kg group | Sham operation group | Model group | DF-521 30 BU/kg group |
| 0 | 100 | 0 | 0 | 100 | 0 | 0 |
| 1 | 0 | 0 | 63.6 | 0 | 54.5 | 81.8 |
| 2 | 0 | 45.5 | 27.3 | 0 | 36.4 | 18.2 |
| 3 | 0 | 36.4 | 9.1 | 0 | 9.1 | 0 |
| 4 | 0 | 18.1 | 0 | — | — | — |

As for the neutrophilic infiltration, the percentage of rats with scores 2-4 of the model group and DF-521 30 BU/kg group was 100.0% and 36.4% respectively. The neutrophil infiltration into a glandular cavity is an indicator of nonbacterial prostatitis. From these results, it can be understood that batroxobin is effective in treating chronic nonbacterial prostatitis.

As for the lymphocyte and plasmacyte infiltration, the percentage of rats having score 2 or 3 (more focal infiltration) in the model group and DF-521 30 BU/kg group was 45.5% and 18.2% respectively. Lymphocyte and plasmacyte infiltration into the stromata is an indicator of chronic nonbacterial prostatitis. From these results, it can be understood that batroxobin is effective in treating chronic nonbacterial prostatitis.

It was confirmed from the above results that batroxobin can treat chronic nonbacterial prostatitis. Furthermore it is thought from the results of this example that batroxobin is effective in improving the voiding symptoms and post micturition symptoms which are associated with clinical chronic nonbacterial prostatitis and a lower urinary tract pain.

Example 3

The Effect of Batroxobin on Benign Prostatic Hyperplasia

1. Experimental Method

Batroxobin (DF-521) was used, which is a product of Beijing Tobishi Pharmaceutical Co., Ltd., China Sesame oil and 17β-Estradiol ($E_2$) were used, which is a product of Sigma Co., Ltd., USA. Testosterone (T) was used, which is a product of Zhejiang Xianju Pharmaceutical Co., Ltd., China $E_2$ and T were used for the establishment of benign prostatic hyperplasia model group.

(1) Experiment Animals and Group Division 13-week-old male Wistar rats, weighing 340-420 g, were purchased from the Beijing Vital River Laboratory Animal Co., Ltd., China The rats were raised in SPF class rooms with a Temperature of 20-25° C., Relative Humidity of 40-70%, Light and Dark Cycle (12 h/12 h). Solid feed sterilized with $^{60}$Co and sterilized water were provided ad libitum (SPF class, Beijing Science Au Corporate Feed Co., Ltd., China) After being quarantined and habituated for one week, the rats were ready to be used for the experiments. 13-week-old male Wistar rats were separated into 3 groups; a sham operation group, a model group, and a DF-521 30 BU/kg group, with 10-11 rats in each group.

(2) Establishment of the Benign Prostatic Hyperplasia Model

Scrotums of rats in the sham operation were only cut open under ether anesthesia (First day of the experiment). The following day the rats were administered a subcutaneous dose of 1 mg/kg of sesame oil on their backs, once a day for a span of 32 consecutive days.

After the rats in the other 2 groups were put under ether anesthesia and castrated (first day of experiment), the next day 50 μg/5000 μg/ml/kg of $E_2$/T was dissolved in sesame oil and administered subcutaneously on their backs once per day for 32 consecutive days in order to create the benign prostatic hyperplasia model.

(3) Dosage Method

Starting from the 14th day of the experiment, the rats administration of saline solution or drugs started. The sham operation and model groups were given intraperitoneal doses of saline solution (5 ml/kg) once every other day. The DF-521 30 BU/kg group was given an intraperitoneal dose of DF-521 30 BU/5 ml/kg once every other day. The administration of a total 19-day span had DF-521 being administered a total of 10 times. The experiment was completed on the 33rd day.

(4) Histopathological Examination

On the 33rd day, the rats were put under ether anesthesia. An EDTA anticoagulant was used to collect blood from the abdominal aorta. The prostate was extracted and the lateral and ventral lobes from prostate were formalin-fixed, paraffin-embedded sections were made according to the conventional method, and hematoxylin-eosin (HE) staining was conducted. Histopathological sections were examined under the microscope.

2. Results (1) Histopathological Findings on the Rat Prostate Gland

Figure 4:
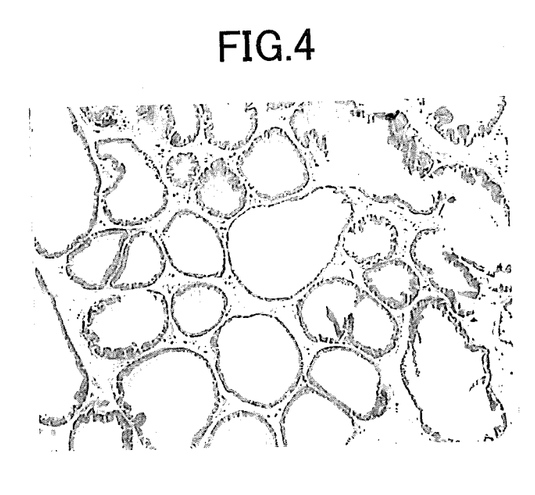
FIG. 4 shows a photomicrograph (×40) of the sham operation group in the experiment on benign prostatic hyperplasia.
Figure 5:
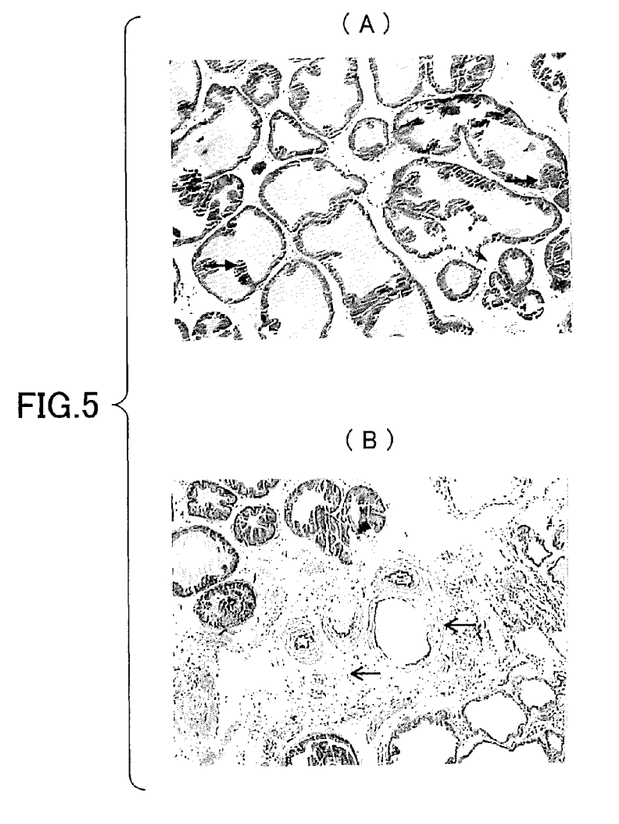
Figure 6:
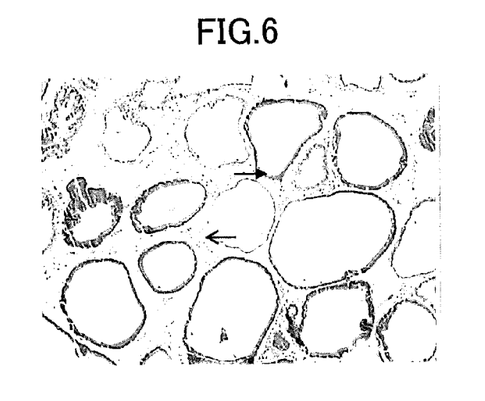
FIG. 6 shows a photomicrograph (×40) of DF-521 30 BU/kg group in the experiment on benign prostatic hyperplasia. A rightward arrow shows a reduced nipple-like thickening in the glandulary epithelium. A leftward arrow shows reduced proliferation and fibrosis in the stromata.

FIG. 4 shows the photomicrograph of the sham operation group. The structure of the prostate was seen as well-defined. The glands were arranged neatly. The proliferation or edema of the stromal and epithelial gland was not observed. FIG. 5A and FIG. 5B show a photomicrograph of the model group. In the model group stromal proliferation was clearly visible. The arrow in FIG. 5A points to the enlargement of glandular cavity and nipple-like thickening in the epithelial glands, and the arrow in FIG. 5B shows the focal fibrosis and minor edema in the stroma. FIG. 6 shows a photomicrograph of the DF-521 30 BU/kg group. The proliferation of the epithelial gland (Rightward arrow) and the stroma as well as fibrosis (Leftward arrow) was reduced when compared to the model group. From these results it can be understood that batroxobin is effective in the treatment of benign prostatic hyperplasia.

(2) Semi-Quantitative Assessment Based on Histopathological Findings

The degree of stromal proliferation and glandular proliferation in prostatic tissue sample of each rat was scored according to the following assessment criteria. The effect of batroxobin on benign prostatic hyperplasia was assessed from this score. The results are shown in Table 6. In Table 6, the value (%) for a group means a percentage of the number of rat having a score relative to the total number of rats in the group.

1) Assessment Criteria for Stromal Proliferation

0: no stromal proliferation. Stromal proliferation was not observed when compared to the Sham operation group.

1: low level stromal proliferation. 10% or less of the total number of glands was folded into single or double layered smooth muscle fiber existing in stroma.

2: middle level stromal proliferation. 10% or less of the total number of glands was folded into multilayered concentric-like smooth muscle fiber existing in stroma.

3: severe level stromal proliferation. 10.20% of the total number of glands was folded into multilayered concentric-like smooth muscle fiber existing in stroma.

2) Assessment Criteria for Glandular Proliferation (Enlargement of Gland or Proliferation of Glandular Epithelium)

0: no glandular proliferation.

1: glandular proliferation was observed in 24.9% or less of the total number of glands.

2: glandular proliferation was observed in 25-49.9% of the total number of glands.

3: glandular proliferation was observed in 50-74.9% of the total number of glands.

4: glandular proliferation was observed in 75% or more of the total number of glands.

TABLE 6

|  | Stromal proliferation (%) | | | Glandular proliferation (%) | | |
| --- | --- | --- | --- | --- | --- | --- |
| Score | Sham operation group | Model group | DF-521 30 BU/kg group | Sham operation group | Model group | DF-521 30 BU/kg group |
| 0 | 100 | 0 | 0 | 100 | 0 | 0 |
| 1 | 0 | 50.0 | 66.7 | 0 | 60.0 | 77.8 |
| 2 | 0 | 40.0 | 33.3 | 0 | 20.0 | 22.2 |
| 3 | 0 | 10.0 | 0 | 0 | 10.0 | 0 |
| 4 | — | — | — | 0 | 10.0 | 0 |

It was observed from these results that 50% of the model group rats tested had middle or severe level of stromal proliferation whereas middle level of stromal proliferation was seen in only 33% of the DF-521 30 BU/kg group. Therefore, it is shown that batroxobin can inhibit the stromal proliferation in benign prostatic hyperplasia.

As for the glandular proliferation, the percentage of rats with a score of 3 or 4 (glandular proliferation was observed in 50% or more of the total number of glands) was 20.0% and 0% for the model group and DF-521 30 BU/kg group respectively. Therefore, it is shown that batroxobin can inhibit the glandular proliferation in benign prostatic hyperplasia.

It can be understood from the aforementioned results that batroxobin is effective in treating benign prostatic hyperplasia. Furthermore, it is thought, based on the examples, that batroxobin is also effective in improving voicing symptoms, post-micturition symptoms and the lower urinary tract pain that accompany benign prostatic hyperplasia.

Example 4

Clinical Effects of Batroxobin on Interstitial Cystitis

1. Experimental Method

Batroxobin (DF-521) was used, which is a product of Beijing Tobishi Pharmaceutical Co., Ltd., China, with a trade name of Dong Ling Di Fu. The data for interstitial cystitis patients was collected from 10 patients originally. However one female patient (No. 01) in the middle of treatment dropped out the study. Ultimately, only the data from 9 patients were collected.

(1) Dosage Method

The first dosage given was 10 BU of DF-521 diluted with 100 ml of physiological saline and administered by intravenous drip for more than one hour. After this, 5 BU of DF-521 was diluted with 100 ml of physiological saline and administered by intravenous drip for more than one hours, once every other day. DF-521 was administered a total of fourteen times.

(2) Selection Criteria

The diagnosis criteria for interstitial cystitis has not been established. The NIDDK (National Institute of Diabetes and Digestive and Kidney Diseases) has announced the criteria for research purpose. However, this criteria are too strict for clinical use. This is because over 60% of interstitial cystitis patients are excluded from this criteria.

Under the situation, this example used the clinical diagnostic criteria based on cystoscopic examination results, which were now considered to be most reasonable and objective observational results for interstitial cystitis. In this example, if a tester meets the following three symptoms 1)-3), the tester was diagnosed as having interstitial cystitis.

1) Symptoms such as pollakiuria, increased voiding, urgency, bladder discomfort and bladder pain
2) Hunner Ulcer or hemorrhaging after hydraulic distension of the bladder are observed in bladder.
3) The above-mentioned symptoms or observations cannot be explained by other diseases and conditions.

(3) Exclusion Criteria

Patients with any one of the following conditions 1)-7) were excluded from testing.
1) The patient with heart, liver, or kidney complications.
2) The patient who has undergone treatment with heparin, low molecular weight heparin, and dicoumarol-like drugs within two weeks prior to the treatment of interstitial cystitis.
3) The patient afflicted with massive cerebral infarction, a tendency for serious hemorrhaging or intracranial hemorrhaging.
4) The patient with active ulcers or hemorrhoids.
5) The patient with a blood pressure higher than 180/100 mmHg.
6) The woman who is pregnant or lactating.
7) The person who is allergic to batroxobin.

(4) Clinical Assessment Indicator

1) Symptoms of increased daytime frequency and nocturia measurement was carried out in 3 consecutive days before treatment and 3 consecutive days after the last administration (Table 7).
2) Interstitial Cystitis Symptom Index (O'Leary-Sant score): This score was counted before and after treatment respectively (Table 8).

O'Leary-Sant score was total of scores for the answers to 4 Problem questions and 4 symptom questions of interstitial cystitis (Table IV, O'Leary M P, Sant G R, Fowler F J Jr, Whitmore K E, Spolarich-Kroll J., The interstitial cystitis symptom index and problem index, Urology 49 (Suppl 5A): 58-63, 1997).

3) QOL score: The scores were counted before and after treatments (Table 8). Answers to questions "If you were to spend the rest of your life with your urinary condition the way it is now, how would you feel?" were given a score.

(5) Clinical Laboratory Test

The values of plasma fibrinogen (FBG), prothrombin time (PT) and activated partial thromboplastin time (APTT) before administration and after treatment with batroxobin (48 hours after the last administration) were examined one time each.

(6) Statistical Analysis

Using the SPSS 13.0 software, the average voided volume and 24-hour voiding frequency, O'Leary-Sant scores and QOL scores before and after treatment were compared and analyzed. When the data conformed to the normal distribution, t-test was used. When the data did not conform to the normal distribution, the rank sum test was used.

2. Results

There were a total of 10 registered patients. There was 1 male and 9 females. All of these patients were selected because they met criteria for interstitial cystitis. One female patient (Patient No. 01) voluntarily discontinued the experiment after 7 rounds of treatment and was not evaluated.

The other 9 patients (Patients No. 02-10) were administered 14 times, and data of these 9 patients were used for the statistical processing.

(1) Average voided volume and 24-hour voiding frequency (the number of voiding occurred during 24 hours) of a patient before and after the batroxobin treatment The 9 patients who received 14 times batroxobin administrations, were evaluated for the average voided volume and 24-hour voiding frequency before and after the batroxobin treatment. The results are shown in Table 7.

TABLE 7

Average voided volume and voiding frequency (Mean ± SD, n = 9)

| Patient No. | Average voided volume (ml) | | | 24-hour period frequency | | |
|---|---|---|---|---|---|---|
| | Before treatment | After treatment | Percent change | Before treatment | After treatment | Percent change |
| 02 | 105.65 | 124.76 | 18.09% | 23 | 21 | −8.70% |
| 03 | 69.52 | 78.78 | 13.32% | 40 | 40 | 0.00% |
| 04 | 103.06 | 118.13 | 14.62% | 17 | 13 | −23.53% |
| 05 | 98.51 | 101.18 | 27.10% | 12 | 11 | −8.33% |
| 06 | 84.76 | 112.03 | 32.17% | 16 | 16 | 0.00% |
| 07 | 188.10 | 200.00 | 6.33% | 13 | 15 | 15.38% |
| 08 | 307.59 | 316.79 | 2.99% | 11 | 14 | 27.27% |
| 09 | 119.71 | 132.38 | 10.58% | 18 | 14 | −22.22% |
| 10 | 144.39 | 128.6 | −10.94% | 14 | 12 | −14.29% |
| Mean value | 135.70 ± 73.27 | 145.85 ± 72.00* | 12.70% | 18.22 ± 8.94 | 17.33 ± 8.97 | −3.82% |

*$p < 0.05$: in comparison to the value of "before treatment"

As shown in Table 7, the average voided volume of "after treatment" (145.85±72.00 ml) was increased in comparison to that of "before treatment" (135.70±73.27 ml). This increase of 12.70% was significant ($p<0.05$). The increase in the average voided volume is thought to be due to the improvement by batroxobin on storage functioning of the bladders of interstitial cystitis patients.

The voiding frequency within the 24-hour period of "after treatment" (17.33±8.97) was less than the value of "before treatment" (18.22±8.94). Small reduction of the voiding frequency (3.82%) was observed in "after treatment" ($p=0.33$).

It is thought that the decrease in voiding frequency (improvement of Increased Daytime Frequency and Nocturia) is due to the aforementioned increase in average voided volume due to the improvement by batroxobin on storage functioning of the bladder.

It can be understood from these results that batroxobin is effective in improving the lower urinary tract symptoms (storage symptoms) that accompany interstitial cystitis.

(2) O'Leary-Sant and QOL Scores of a Patient Before and after the Batroxobin Treatment The 9 patients who received 14 times batroxobin administrations, were evaluated for the O'Leary-Sant and QOL scores before and after the batroxobin treatment and the degree of improvement on the scores was compared.

TABLE 8

Interstitial Cystitis Index (O' Leary-Sant) score and QOL score (Mean ± SD, n = 9)

| Patient No. | O'Leary-Sant score | | | QOL score | | |
|---|---|---|---|---|---|---|
| | Before treatment | After treatment | Percent change | Before treatment | After treatment | Percent change |
| 02 | 15 | 13 | −13.33% | 4 | 4 | 0.00% |
| 03 | 27 | 28 | 3.70% | 6 | 6 | 0.00% |
| 04 | 24 | 14 | −41.67% | 6 | 4 | −33.33% |
| 05 | 25 | 21 | −16.00% | 5 | 4 | −20.00% |
| 06 | 27 | 22 | −18.52% | 5 | 3 | −40.00% |
| 07 | 26 | 23 | −11.54% | 6 | 4 | −33.33% |
| 08 | 20 | 18 | −10.00% | 5 | 4 | −20.00% |
| 09 | 24 | 19 | −20.83% | 5 | 3 | −40.00% |
| 10 | 19 | 14 | −26.32% | 6 | 4 | −33.33% |
| Mean | 23.00 ± 4.12 | 19.11 ± 4.96* | −17.17% | 5.33 ± 0.71 | 4.00 ± 0.87* | −24.44% |

*$p < 0.05$: in comparison to the value of "before treatment"

O'Leary-Sant score:
0-15 = low level
16-23 = middle level
24-35 = severe level

QOL score:
0 = best
1 = satisfactory
2 = somewhat good
3 = fair
4 = not good
5 = worse
6 = worst As shown in Table 8, the O'Leary-Sant score of "after treatment" (19.11±4.96) was decreased in comparison to that of "before treatment" (23.00±4.12). This reduction of 17.17% was significant ($p<0.05$). This result indicates that batroxobin significantly improved the O'Leary score which evaluates clinical symptoms associated with interstitial cystitis such as pollakiuria, increased voiding, urgency and bladder pain.

The QOL score of "after treatment" (4.00±0.87) was decreased in comparison to that of "before treatment" (5.33±0.71). This reduction of 24.44% was significant ($p<0.05$).

It can be understood from the above results that batroxobin is effective in improving the patient's QOL as well as the lower urinary tract symptoms that is associated with interstitial cystitis.

(3) Clinical Laboratory Test Values of a Patient Before and after the Batroxobin Treatment The 9 patients who received 14 times batroxobin administrations, were evaluated for plasma fibrinogen (FBG), prothrombin time (PT) and activated partial thromboplastin time (APTT) before the batroxobin treatment and after the batroxobin treatment (48 hours after the last administration).

These results indicate FBG of "before treatment" was 3.24±1.04 g/L and FBG of "after treatment" was 2.33±0.76 g/L and the reduction was significant ($p<0.05$). On the other hand, PT of "before treatment" was 12.18±1.01 seconds and PT of "after treatment" was 12.57±1.04 seconds. APTT of "before treatment" was 31.48±5.41 seconds and APTT of "after treatment" was 34.21±4.74. As for PT and APTT, there was no significant difference between "before treatment" and "after treatment." The p-value for PT was 0.397. The p-value for APTT was 0.085.

Based on the above-mentioned results, it was confirmed that there was no possibility of bleeding as a side effect occurring by defibrinogenating effect of batroxobin in interstitial cystitis patients.

INDUSTRIAL APPLICABILITY

The present invention can be used to treat various lower urinary tract diseases such as cystitis, prostatitis and benign prostatic hyperplasia; and improve lower urinary symptoms associated with the lower urinary tract disease.

The invention claimed is:

1. A treatment method for improving a lower urinary tract symptom associated with a lower urinary tract disease, the method comprising the step of administering a thrombin-like enzyme selected from the group consisting of batroxobin, ancrod and crotalase to a patient in need thereof exhibiting the lower urinary tract symptom, thereby improving said symptom, wherein the symptom is selected from the group consisting of storage symptom, voiding symptom and post micturition symptom.

2. The method according to claim 1, wherein the thrombin-like enzyme is batroxobin.

3. The method according to claim 1, wherein the symptom is associated with a lower urinary tract disease selected from the group consisting of cystitis, prostatitis and benign prostatic hyperplasia.

4. The method according to claim 1, wherein the symptom is associated with a lower urinary tract disease selected from the group consisting of hemorrhagic cystitis, interstitial cystitis, chronic nonbacterial prostatitis and benign prostatic hyperplasia.

5. A treatment method for improving a lower urinary tract pain associated with a lower urinary tract disease, the method comprising the step of administering a thrombin-like enzyme selected from the group consisting of batroxobin, ancrod and crotalase to a patient in need thereof exhibiting the lower urinary tract pain, thereby improving the pain.

6. The method according to claim 5, wherein the thrombin-like enzyme is batroxobin.

7. The method according to claim 5, wherein the pain is associated with a lower urinary tract disease selected from the group consisting of cystitis, prostatitis and benign prostatic hyperplasia.

8. The method according to claim 5, wherein the pain is associated with a lower urinary tract disease selected from the group consisting of hemorrhagic cystitis, interstitial cystitis, chronic nonbacterial prostatitis and benign prostatic hyperplasia.

9. The method according to claim 5, wherein the lower urinary tract pain is selected from the group consisting of bladder pain and urethral pain.

\* \* \* \* \*